(12) United States Patent
Son et al.

(10) Patent No.: US 9,952,169 B2
(45) Date of Patent: Apr. 24, 2018

(54) METHOD OF MEASURING BIOLOGICAL SAMPLE PROPERTIES AND BIOLOGICAL SAMPLE PROPERTY MEASURING APPARATUS

(71) Applicants: SAMSUNG ELECTRONICS CO., LTD., Suwon-si (KR); INDUSTRY-ACADEMIC COOPERATION FOUNDATION, YONSEI UNIVERSITY, Seoul (KR)

(72) Inventors: Sang Uk Son, Yongin-Si (KR); Duck Hwan Kim, Goyang-Si (KR); In Sang Song, Osan-Si (KR); Seong Chan Jun, Seoul (KR); Ho Soo Park, Yongin-si (KR); Jea Shik Shin, Hwaseong-si (KR); Moon Chul Lee, Seongnam-si (KR)

(73) Assignees: Samsung Electronics Co., Ltd., Suwon-si (KR); Industry-Academic Cooperation Foundation, Yonsei University, Seoul (KR)

( * ) Notice: Subject to any disclaimer, the term of this patent is extended or adjusted under 35 U.S.C. 154(b) by 152 days.

(21) Appl. No.: 14/881,819

(22) Filed: Oct. 13, 2015

(65) Prior Publication Data
US 2016/0033435 A1     Feb. 4, 2016

Related U.S. Application Data

(62) Division of application No. 13/760,114, filed on Feb. 6, 2013, now abandoned.

(30) Foreign Application Priority Data

May 10, 2012   (KR) .................. 10-2012-0049543

(51) Int. Cl.
*G01N 27/08*     (2006.01)
*G01N 27/02*     (2006.01)
(Continued)

(52) U.S. Cl.
CPC .............. *G01N 27/08* (2013.01); *A61B 5/05* (2013.01); *A61B 5/053* (2013.01); *G01N 27/02* (2013.01);
(Continued)

(58) Field of Classification Search
CPC ...... G01N 27/08; G01N 27/226; G01N 27/07; G01N 27/02; A61B 5/05; A61B 5/053; A61B 5/14532; A61B 5/14546
See application file for complete search history.

(56) References Cited

U.S. PATENT DOCUMENTS 5,429,734 A * 7/1995 Gajar ............... G01N 27/44756
                                                                    204/603
5,436,565 A * 7/1995 Gammell ............ G01N 27/221
                                                                    324/679

(Continued)

FOREIGN PATENT DOCUMENTS

KR    10-2005-0050425 A    5/2005
KR    10-2009-0085913 A    8/2009

(Continued)

OTHER PUBLICATIONS

IP Kang A study on Sensing Characteristics of Carbon Nanotube Smart Composite Nano Sensor Based on Electrical Impedance Measurement, 2009, 7 pages in Korean.

(Continued)

*Primary Examiner* — Melanie Yu Brown
(74) *Attorney, Agent, or Firm* — NSIP Law

(57) ABSTRACT

A method of measuring biological sample properties and a biological sample property measuring apparatus is provided. A method of measuring biological sample properties includes disposing a biomaterial to contact a sensing unit, detecting a radio frequency (RF) signal flowing through the (Continued)

sensing unit, and obtaining an RF property indicator of the biomaterial based on the detected RF signal.

10 Claims, 7 Drawing Sheets

(51) Int. Cl.
    *A61B 5/053*    (2006.01)
    *A61B 5/05*     (2006.01)
    *G01N 27/07*    (2006.01)
    *G01N 27/22*    (2006.01)
    *A61B 5/145*    (2006.01)

(52) U.S. Cl.
    CPC .......... *G01N 27/07* (2013.01); *G01N 27/226* (2013.01); *A61B 5/14532* (2013.01); *A61B 5/14546* (2013.01)

(56) References Cited

U.S. PATENT DOCUMENTS

| | | | |
|---|---|---|---|
| 6,169,394 B1 * | 1/2001 | Frazier | G01N 27/4473 324/692 |
| 7,898,005 B2 | 3/2011 | Yang et al. | |
| 8,329,437 B1 * | 12/2012 | Ayliffe | G01N 15/1056 422/68.1 |
| 2003/0127329 A1 * | 7/2003 | DeVoe | G01N 27/44752 204/454 |
| 2005/0112621 A1 * | 5/2005 | Kim | G01N 29/022 435/6.19 |
| 2010/0327874 A1 * | 12/2010 | Liu | G01N 33/48721 324/464 |

FOREIGN PATENT DOCUMENTS

| | | |
|---|---|---|
| KR | 10-2010-0081786 A | 7/2010 |
| KR | 10-2010-0131195 A | 12/2010 |
| KR | 10-2011-0104245 A | 9/2011 |
| KR | 10-2011-0112327 | 10/2011 |
| KR | 10-2011-0124855 A | 11/2011 |

OTHER PUBLICATIONS

Korean Office Action dated Nov. 20, 2017, in corresponding Korean Application No. 10-2012-0049543 (8 pages in English, 8 pages in Korean).

* cited by examiner

300

METHOD OF MEASURING BIOLOGICAL SAMPLE PROPERTIES AND BIOLOGICAL SAMPLE PROPERTY MEASURING APPARATUS

CROSS-REFERENCE TO RELATED APPLICATIONS

This present application is a Divisional of U.S. patent application Ser. No. 13/760,114, filed Feb. 6, 2013, which claims the benefit under 35 U.S.C. § 119(a) of Korean Patent Application No. 10-2012-0049543, filed on May 10, 2012, in the Korean Intellectual Property Office, the entire disclosure of which is incorporated herein by reference for all purposes.

BACKGROUND

1. Field

The following description relates to a method of measuring biological sample properties and a biological sample property measuring apparatus.

2. Description of Related Art

A radio frequency (RF) is used in radio broadcasting, wireless broadcasting, wireless communication, and other applications known to one of ordinary skill in the art. An example of an RF refers to a range of frequencies corresponding to a frequency of an electrical signal.

Examples of a biological sample include a protein and a biological tissue. Properties of the biological sample may be measured using a biosensor. Generally, manufacturing of a biosensor and performing an analysis using a biosensor requires costly equipment. For example, in order to measure properties of a biological sample using a biosensor, complex pre-treatment of the biological sample is required.

SUMMARY

In one general aspect, a method of measuring biological sample properties is provided, the method including disposing a biomaterial to contact a sensing unit, detecting a radio frequency (RF) signal flowing through the sensing unit, and obtaining an RF property indicator of the biomaterial based on the detected RF signal.

The method may further include that the biomaterial is in vivo or in vitro contact with the sensing unit.

The method may further include that the biomaterial includes a fluid in continuous contact with the sensing unit while flowing through a microchannel.

The method may further include that the obtaining of the RF property indicator includes obtaining the RF property indicator iteratively from a time at which the fluid begins flowing on the sensing unit, and detecting a change in the iteratively obtained RF property indicator in real time.

The method may further include that the biomaterial includes a biological sample, and the detecting of the RF signal is performed after a change in a state of the biological sample occurs.

The method may further include that the RF property indicator includes one or more from the group consisting of an impedance, an inductance, a conductance, a capacitance, and a frequency.

The method may further include that the biomaterial includes one or more from the group consisting of a cell, an organelle, a body fluid, deoxyribonucleic acid (DNA), ribonucleic acid (RNA), blood, plasma, glucose, glycated hemoglobin, cholesterol, a cancer cell, an antigen, an antibody, an influenza, protein, and a biological tissue.

The method may further include that the sensing unit includes a mono-layered or multi-layered carbon-based material.

In another general aspect, a biological sample property measuring apparatus includes a sensing unit configured to contact a biomaterial, an electrode unit configured to detect a radio frequency (RF) signal flowing through the sensing unit, and a probe unit configured to obtain an RF property indicator of the biomaterial based on the detected RF signal.

The apparatus may further include that the biomaterial is in vivo or in vitro contact with the sensing unit.

The apparatus may further include that the biomaterial includes a fluid in continuous contact with the sensing unit while flowing through a microchannel.

The apparatus may further include that the RF property indicator includes one or more of the group consisting of an impedance, an inductance, a conductance, a capacitance, and a frequency.

The apparatus may further include that the biomaterial includes one or more of the group consisting of a cell, an organelle, a body fluid, deoxyribonucleic acid (DNA), ribonucleic acid (RNA), blood, plasma, glucose, glycated hemoglobin, cholesterol, a cancer cell, an antigen, an antibody, an influenza, protein, and a biological tissue.

The apparatus may further include that the sensing unit includes a mono-layered or multi-layered carbon-based material.

In yet another general aspect, a biological sample property measuring apparatus includes a microchannel configured to provide a flow channel for a biological sample; a sensing unit on the flow channel, the sensing unit being configured to contact the biological sample, a first signal electrode configured to transmit a radio frequency (RF) signal to a first area of the sensing unit, a second signal electrode configured to transmit the RF signal to a second area of the sensing unit, an RF property indicator between the first area of the sensing unit and the second area of the sensing unit being supplied to a probe unit, and a ground electrode configured to ground the RF signal.

The apparatus may further include that the probe unit includes a first probe and a second probe, the first probe including a first tip and a second tip, the first tip of the first probe contacting the first signal electrode, the second tip of the first probe contacting the ground electrode, the second probe including a first tip and a second tip, the first tip of the second probe contacting the second signal electrode, the second tip of the second probe contacting the ground electrode.

The apparatus may further include a measuring unit configured to supply the RF signal to the first signal electrode and the second signal electrode through the probe unit and receive the RF signal from the sensing unit through the probe unit.

The apparatus may further include that the microchannel includes a polydimethysiloxane (PDMS) layer configured to prevent leakage of the biological sample.

The apparatus may further include a substrate on which the microchannel, the sensing unit, the first signal electrode, the second signal electrode, and the ground electrode are formed.

Other features and aspects will be apparent from the following detailed description, the drawings, and the claims.

Figure 1:
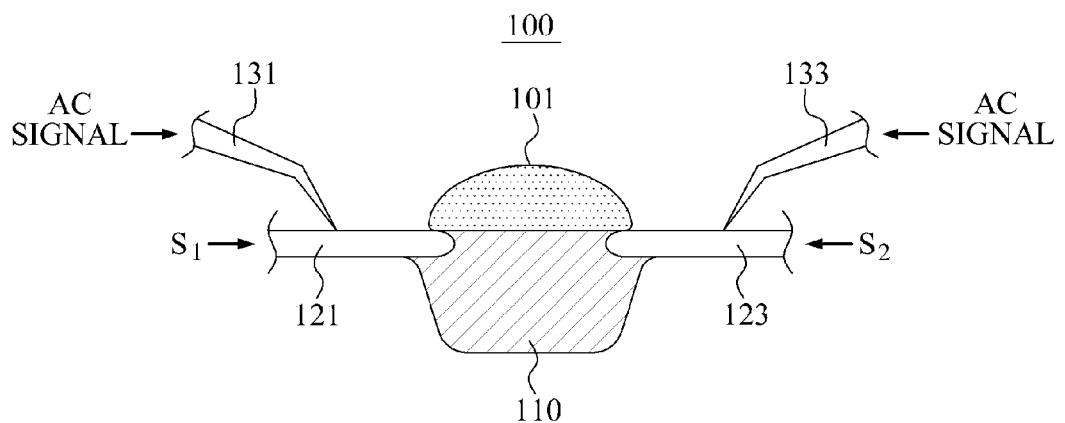
FIG. 1 is a cross-sectional view illustrating an example of a biological sample property measuring apparatus.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, description of well-known functions and constructions may be omitted for increased clarity and conciseness.

It is understood that the features of the present disclosure may be embodied in different forms and should not be constructed as limited to the example embodiment(s) set forth herein. Rather, embodiment(s) are provided so that this disclosure will be thorough and complete, and will convey the full scope of the present disclosure to those skilled in the art. The drawings may not be necessarily to scale, and, in some instances, proportions may have been exaggerated in order to clearly illustrate features of the embodiment(s). When a first layer is referred to as being "on" a second layer or "on" a substrate, it may not only refer to a case where the first layer is formed directly on the second layer or the substrate but may also refer to a case where a third layer exists between the first layer and the second layer or the substrate.

FIG. 1 is a cross-sectional view illustrating an example of a biological sample property measuring apparatus 100. Referring to the example illustrated in FIG. 1, the biological sample property measuring apparatus 100 includes a sensing unit 110, an electrode unit 121 and 123, and a probe unit 131 and 133.

In this example, the sensing unit 110 corresponds to a sensor to sense a biomaterial 101, which is absorbed in the sensing unit 110 or in contact with the sensing unit 110. In the instance in which the biomaterial 101 is in contact with the sensing unit 110, the contact may be maintained for a predetermined period. In an additional example, the biomaterial 101 is in continuous contact with a surface of the sensing unit 110 while flowing through the sensing unit 110 in a fluid or solution.

In an example, the sensing unit 110 includes a monolayered or multi-layered carbon-based material. In a further example, the sensing unit 110 includes a carbon-based nanomaterial. The carbon-based nanomaterial may include, for example, graphene and a carbon nano tube (CNT).

In an example, radio frequency (RF) properties of the sensing unit 110 change before and after contact with the biomaterial 101. In this example, the RF properties are measured in real time while a fluid or solution is flowing through the sensing unit 110.

An example of the biological sample property measuring apparatus 100 obtains an RF property indicator of the biomaterial 101 by measuring the RF properties of the sensing unit 110. In an example, the RF property indicator is transmitted to and analyzed by a measuring unit (not shown). In another example, a measured value of the RF property indicator or an amount of change in the RF property indicator is used to analyze the biomaterial 101. That is, the physical properties of the biomaterial 101 are measured through RF analysis. An example of the RF analysis includes extracting each of indicators including impedance, inductance, conductance, and capacitance from scattering parameters (S-parameters) independently, and analyzing the extracted indicators.

In an example, impedance blocks a flow of an alternating current (AC). In another example, impedance corresponds to a relative amplitude of current and voltage, and a relative phase of current and voltage. When an AC flows in a circuit, no difference between impedance and resistance exists. That is, a phase angle of an AC is zero. In an example, the impedance is detected through analysis of the S-parameters. In another example, the S-parameters are detected using the probe unit 131 and 133.

In the example illustrated in FIG. 1, the S-parameters are obtained by detecting an input and an output of the RF signal at $S_1$ and $S_2$. That is, the S-parameters include a signal loss rate $S_{11}$ at $S_1$, a signal transmission rate $S_{12}$ from $S_1$ to $S_2$, a signal transmission rate $S_{21}$ from $S_2$ to $S_1$, and a signal loss rate $S_{22}$ at $S_2$. In an example of this instance, $S_{12}$ and $S_{21}$ have similar characteristics. By analyzing $S_{11}$, $S_{22}$, $S_{12}$, and $S_{21}$, three factors of impedance, capacitance, inductance, and resistance may be each extracted, and a change in impedance may be displayed through the measuring unit in real time.

The electrode unit 121 and 123 includes a first signal electrode 121 and a second signal electrode 123. In an example, the electrode unit 121 and 123 detects detect the RF signal flowing through the sensing unit 110. As is shown in the example illustrated in FIG. 1, the first signal electrode 121 and the second signal electrode 123 are separated from one another by a predetermined distance, and are in contact with both sides of the sensing unit 110. For conciseness and ease of description, an area of the sensing unit 110 disposed to be in contact with the first signal electrode 121 is hereinafter referred to as a first area of the sensing unit 110, and an area of the sensing unit 110 disposed to be in contact with the second signal electrode 123 is referred to as a second area of the sensing unit 110.

In an example, to measure the RF properties of the sensing unit 110, the RF signal is supplied to the first signal electrode 121 and the second signal electrode 123. In a further example, the RF signal is supplied to the first signal electrode 121 and the second signal electrode 123 through the probe unit 131 and 133. Since the S-parameters are obtained by detecting an input and an output of the RF signal, the RF signal flowing through the sensing unit 110 is detected by supplying the RF signal to the first signal electrode 121 and the second signal electrode 123.

The probe unit 131 and 133 includes probe tips 131 and 133 and, in an example, obtains an RF property indicator of the biomaterial 101 based on the RF signal detected through the electrode unit. That is, in this example, the probe unit 131 and 133 obtains the RF property indicator of the biomaterial 101 indirectly by measuring the RF properties of the sensing unit 110 that are in contact with the biomaterial 101. In this instance, the RF property indicator includes one or more of an impedance, an inductance, a conductance, a capacitance, and a frequency. In an additional example, the RF property indicator includes an AC property.

In the example illustrated in FIG. 1, the sensing unit 110 and the electrode unit 121 and 123 excluding the probe unit 131 and 133 may be referred to as a "biosensor".

Further, in the example illustrated in FIG. 1, dielectrophoresis (DEP) is used as a method of forming the sensing unit 110 between the first signal electrode 121 and the second signal electrode 123. An example of the DEP method includes pouring a solution having a particulate carbon-based material into a space between the first signal electrode 121 and the second signal electrode 123 and applying an AC to the first signal electrode 121 and the second signal electrode 123.

In this instance, due to a difference in dielectric constant between the liquid and the particulate carbon-based material, the particulate carbon-based material is concentrated between the first signal electrode 121 and the second signal electrode 123. In an example, subsequent steps of appropriate drying and heating serve to enhance the mechanical and electrical adhesive performance of the carbon-based material.

In additional examples, a recovery process is used to strengthen bonds between the nanomaterials and between the nanomaterial and the electrodes 121 and 123. An example of recovery process includes putting the biosensor in an aqueous solution of hydrazine, followed by heating at about 100° C. In additional examples, the recovery process includes an annealing process to improve the contact characteristics between the electrodes 121 and 123 and the nanomaterial. Various conditions may be applied to the recovery process in terms of a heating rate, a high temperature, and a duration of maintaining the high temperature.

In an example, the biomaterial 101 includes one or more of a cell, an organelle, a body fluid, deoxyribonucleic acid (DNA), ribonucleic acid (RNA), blood, plasma, glucose, glycated hemoglobin, cholesterol, a cancer cell, an antigen, an antibody, an influenza, protein, and a biological tissue. In this instance, the biomaterial 101 is disposed to be in vivo or in vitro contact with the sensing unit 110. In another example, the sensor unit 110 is disposed to be in contact with blood and other biomaterial known to one of ordinary skill in the art by implanting the biosensor in a body. In additional examples, after a collected biological sample is pre-treated, the collected biological sample is poured or placed on the sensing unit 110 to contact the sensing unit 110. That is, according to the examples suggested herein, the properties of the biomaterial or the sample is measured through implantation in a body.

In additional examples, the biomaterial 101 includes a fluid, and the fluid is in continuous contact with the sensing unit 110 while flowing through a microchannel (not shown). A detailed description of the microchannel is provided later with reference to FIGS. 2 through 7. In this instance, the obtaining of the RF property indicator includes obtaining the RF property indicator iteratively from a time at which the fluid begins flowing on the sensing unit 110, and detecting a change in the iteratively obtained RF property indicator in real time. In further examples, after a change in the state of the collected biological sample poured into the sensing unit 110 occurs, the RF signal is detected. In one of these examples, the RF properties are measured after the state of the collected biological sample changes from a solid state to a liquid state, and from a liquid state to a solid state.

In an example of the RF analysis described through the example illustrated in FIG. 1, graphene is included in the carbon nanomaterial to increase current flow and an electron migration rate. In an another example, the carbon-based nanomaterial is applied to a biosensor and various RF property indicators are used to analyze properties of a biomaterial and changes in the properties of the biomaterial.

Figure 2:
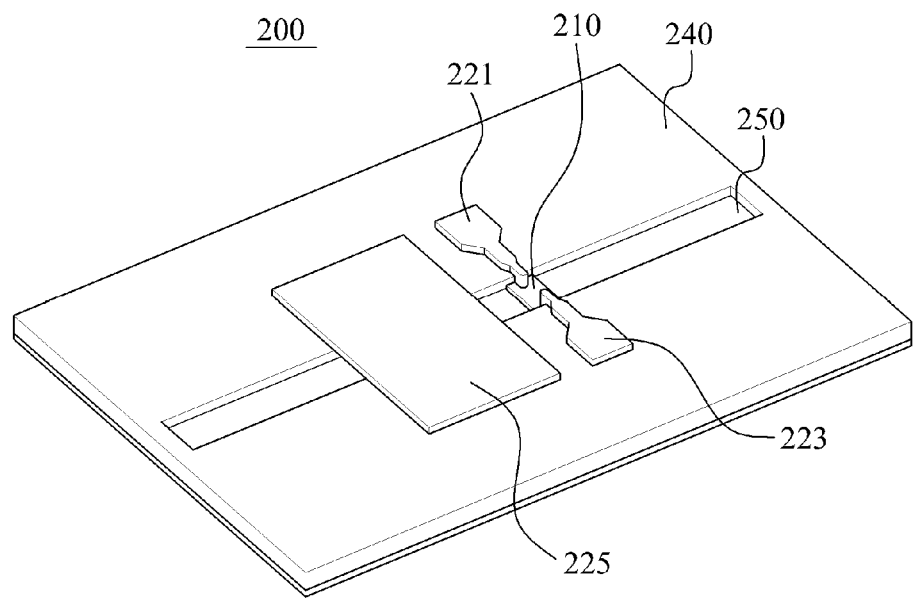
FIG. 2 is a view illustrating another example of a biological sample property measuring apparatus.

FIG. 2 is a view illustrating another example of a biological sample property measuring apparatus 200. Referring to the example illustrated in FIG. 2, the biological sample property measuring apparatus 200 includes a sensing unit 210, a first signal electrode 221, a second signal electrode 223, a ground electrode 225, a substrate 240, and a microchannel 250. The sensing unit 210, the first signal electrode 221, the second signal electrode 223, the ground electrode 225, and the microchannel 250 are formed on the substrate 240.

In various examples, several components of the example illustrated in FIG. 2 perform the same functions as components described with reference to FIG. 1 having the same names. Throughout descriptions provided with reference to examples illustrated in FIGS. 3 through 7, unless otherwise described, the components having the same names as aforementioned will be understood to perform the same functions and be made of the same material.

In an example, the microchannel 250 provides a flow channel for a biological sample. That is, in an example, a liquid-type sample flows along the microchannel 250. Referring to the example illustrated in FIG. 2, the sensing unit 210 is formed at a predetermined location of the microchannel 250. Accordingly, the sensing unit 210 is formed on the flow channel to be in contact with the biological sample.

In an example, the biological sample property measuring apparatus 200 has an area of 1 mm$^2$ or less. Accordingly, the biological sample property measuring apparatus 200 is implantable in a body.

The example illustrated in FIG. 2 may be referred to as a "biosensor". A method of manufacturing a biosensor of FIG. 2 is described with reference to FIG. 5.

Figure 3:
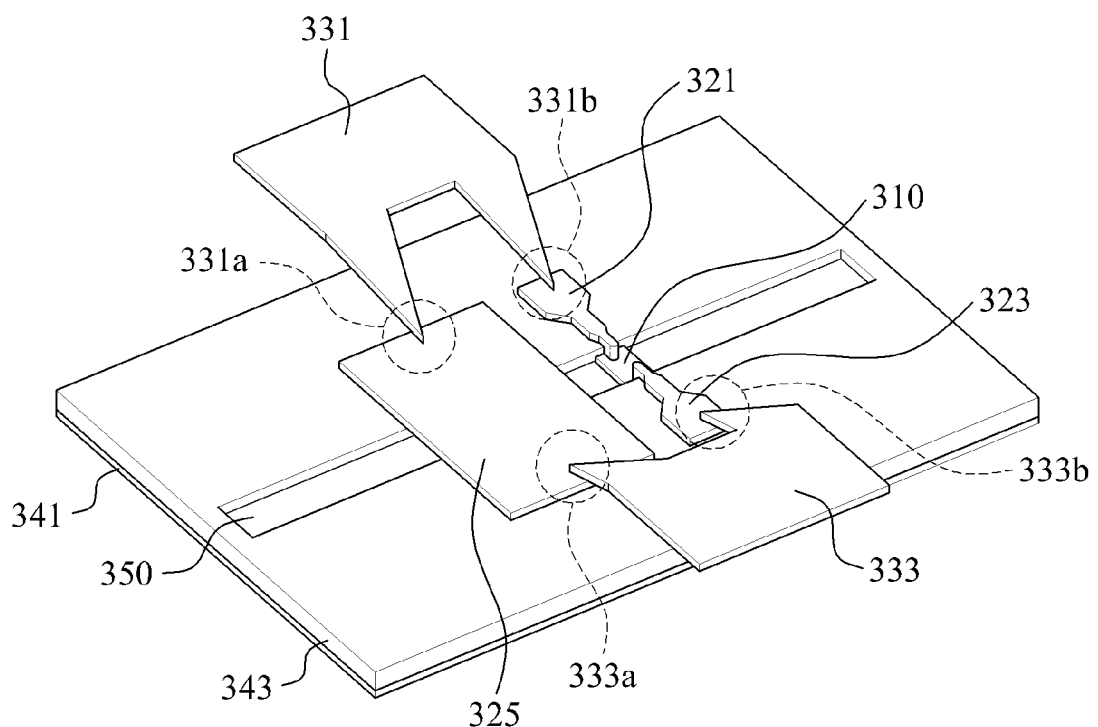
FIG. 3 is a view illustrating still another example of a biological sample property measuring apparatus.

FIG. 3 is a view illustrating still another example of a biological sample property measuring apparatus 300. The biological sample property measuring apparatus 300 described through the example illustrated in FIG. 3 includes a probe unit 331 and 333 when compared to the configuration of the example illustrated in FIG. 2.

Referring to the example illustrated in FIG. 3, the biological sample property measuring apparatus 300 includes a sensing unit 310, a first signal electrode 321, a second signal electrode 323, a ground electrode 325, a probe unit 331 and 333, a substrate 341, and a microchannel 350. The sensing unit 310, the first signal electrode 321, the second signal electrode 323, the ground electrode 325, and the microchannel 350 are formed on the substrate 341. In an example, the substrate 341 includes a silicon wafer. In another example, an insulating layer 343 is formed on the silicon wafer. In a further example, the insulating layer 343 includes silicon dioxide.

In an example, the microchannel 350 provides a flow channel for a biological sample. In the example illustrated in FIG. 3, the sensing unit 310 is formed on the flow channel to be in contact with the biological sample. The first signal electrode 321 is in contact with a first area of the sensing unit 310 and, in an example, transmits an RF signal to the first area of the sensing unit 310. The second signal electrode 323 is in contact with a second area of the sensing unit 310 and, in another example, transmits an RF signal to the second area of the sensing unit 310. In a further example, the ground electrode 325 grounds the RF signal.

In an example, an RF property indicator between the first area of the sensing unit 310 and the second area of the sensing unit 310 is supplied to the probe unit 331 and 333 through the first signal electrode 321 and the second signal electrode 323. The probe unit 331 and 333 includes a first probe tip 331 including a tip 331b contacting with the first signal electrode 321 and a tip 331a contacting with the ground electrode 325. In addition, the probe unit 331 and 333 includes a second probe tip 333 including a tip 333b contacting the second signal electrode 323 and a tip 333a contacting the ground electrode 325.

Figure 4:
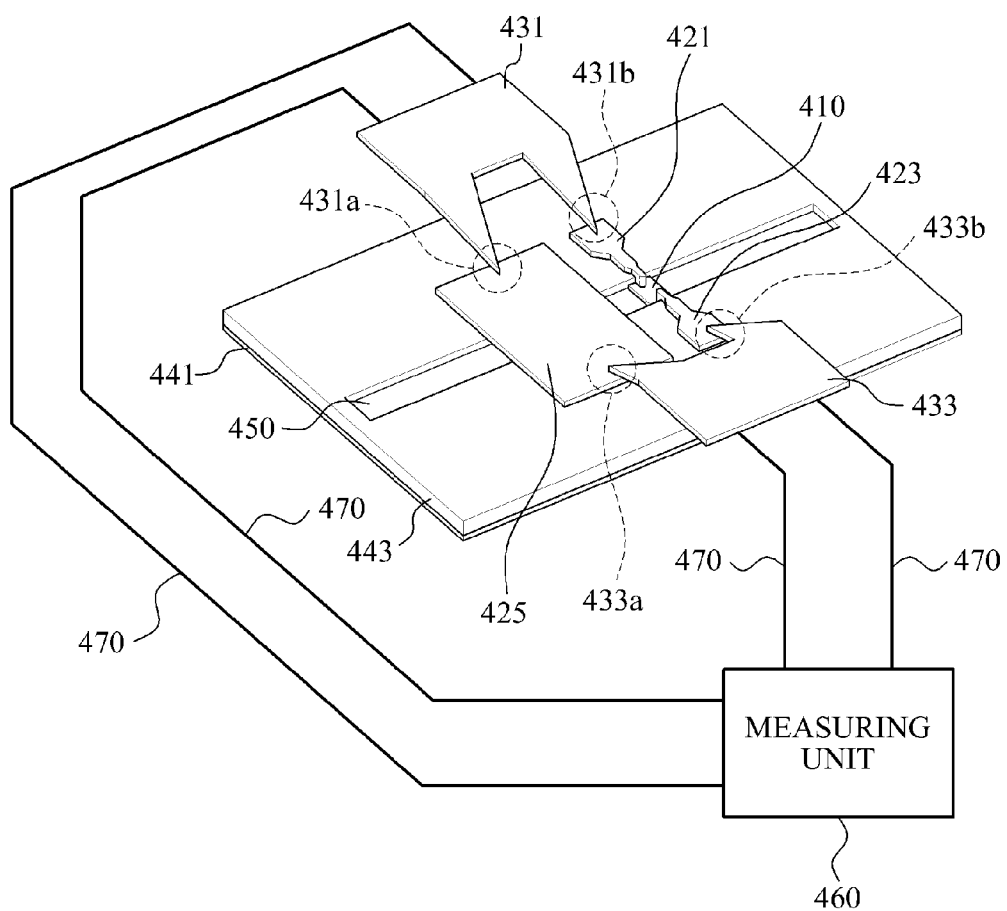
FIG. 4 is a view illustrating yet another example of a biological sample property measuring apparatus.

FIG. 4 is a view illustrating yet another example of a biological sample property measuring apparatus 400. Referring to the example illustrated in FIG. 4, the biological sample property measuring apparatus 400 includes a sensing unit 410, a first signal electrode 421, a second signal electrode 423, a probe unit 431 and 433, a measuring unit 460, and a cable 470. In an example, the measuring unit 460 supplies an RF signal to the first signal electrode 421 and the second signal electrode 423 through the probe unit 431 and 433, respectively, and receives the RF signal from the sensing unit 410 through the probe unit 431 and 433. The measuring unit 460 is connected to the probe unit 431 and 433 via a cable 470.

In an example not shown, the measuring unit 460 is connected to the probe unit 431 and 433 via a wireless channel. Although not shown in the example illustrated in FIG. 4, an example of the measuring unit 460 includes one or more of a display and an input/output device.

In additional examples, a frequency of the RF signal supplied to the first signal electrode 421 and the second signal electrode 423 has a fixed value, or gradually increases. That is, in an example, the measuring unit 460 measures RF property indicators while increasing the frequency of the RF signal. An example of the RF analysis using S-parameters uses one or more of various analysis factors, such as, a change in frequency property, a signal amplitude, an impedance, an inductance, a conductance, and a capacitance.

FIGS. 5A through 5F are views illustrating an example of a method of manufacturing a biosensor of a biological sample property measuring apparatus.

Figure 5A:
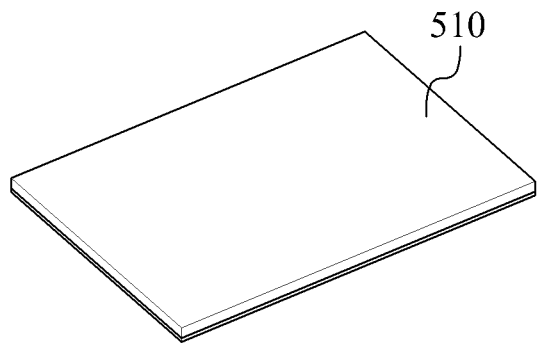
FIGS. 5A through 5F are views illustrating an example of a method of manufacturing a biosensor of a biological sample property measuring apparatus.

FIG. 5A is a view illustrating an example of a process of fabricating a substrate 510, such as a wafer. In an example, the process of fabricating the substrate 510 includes exposure using an electrode-engraved mask after deposition of a predetermined thickness of a negative photoresist layer on the substrate 510.

Figure 5B:
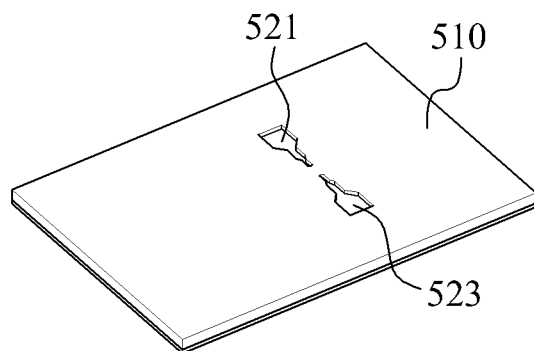

FIG. 5B is a view illustrating an example of the substrate 510 from which the negative photoresist layer is removed after an etching process. Signal electrode-shaped patterns 521 and 523 are formed and etched on the negative photoresist layer. In an example, the distance between the patterns 521 and 523 is in a range between 10 μm to 20 μm. In additional examples, the distance between the signal electrode patterns 521 and 523 is variously determined depending on a size or properties of a sample to be measured. In a further example, the etching process includes dry etching and wet etching. In another example, both of the dry etching and wet etching is used in the etching process. That is, in an example, an etch depth is adjusted by varying a wet etching time and a dry etching time. The etch depth may be, for example, 200 nm.

Figure 5C:
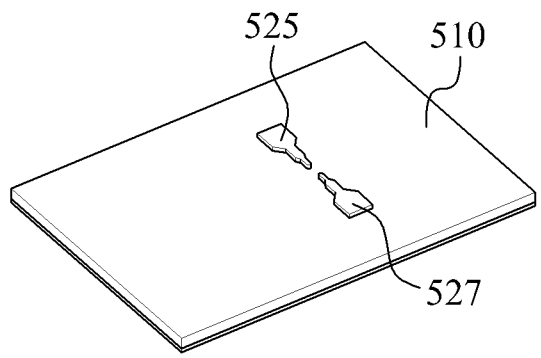

FIG. 5C is a view illustrating an example of the etched substrate 510 on which signal electrodes 525 and 527 are deposited. In an example, a deposition process includes deposition of the signal electrodes 525 and 527 using gold. In a further example, gold is deposited at a height greater than the etch depth. In an additional example, the height of the signal electrodes 525 and 527 is determined to be 400 nm or more.

Figure 5D:
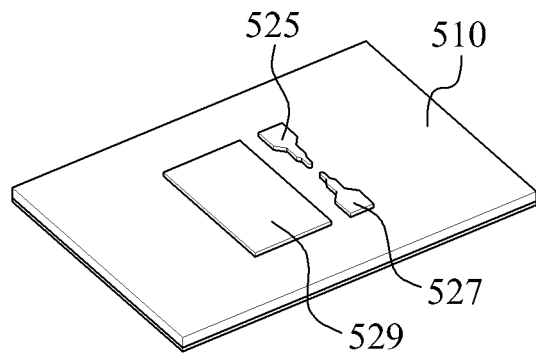

FIG. 5D is a view illustrating an example of the substrate 510 on which a ground electrode 529 is deposited. In an example, a deposition process of the ground electrode 529 includes exposure using a patterned mask by a photolithography process and deposition of the ground electrode 529.

Figure 5E:
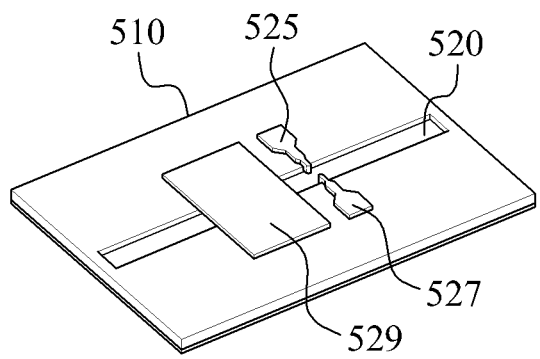

FIG. 5E is a view illustrating an example of the substrate 510 on which a channel 520 is formed. In an example, wet etching using a photolithography process is used to form the channel 520 intersecting the electrodes 525 and 527.

Figure 5F:
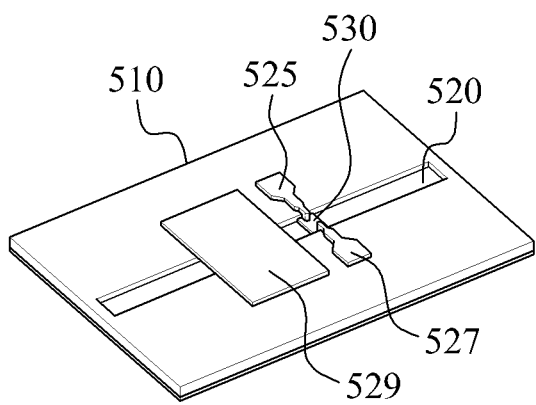

FIG. 5F is a view illustrating an example of the substrate 510 on which a sensing unit 530 is formed between the signal electrodes 525 and 527. In an example, the sensing unit 530 is formed between the signal electrodes 525 and 527 using a DEP method. In an additional example, the sensing unit 530 is formed by depositing a carbon-based film between the signal electrodes 525 and 527, followed by patterning. A method of forming the sensing unit 530 may use various technologies, for example, a stamping technology, a lift-off technology, and other technologies known to one of ordinary skill in the art.

Figure 6:
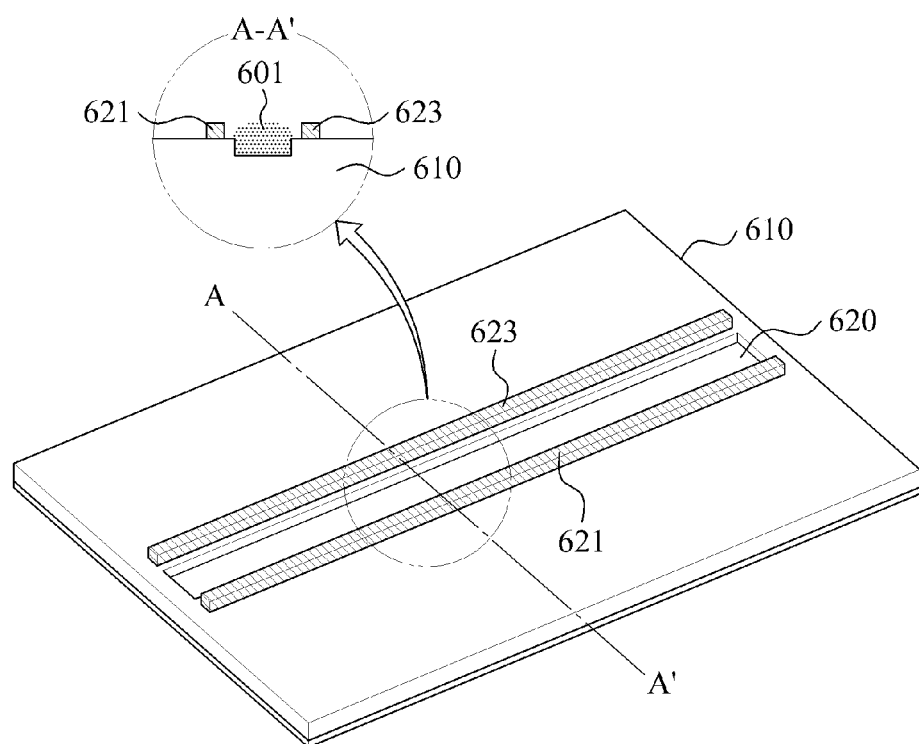
FIG. 6 is a view illustrating an example of a microchannel of a biological sample property measuring apparatus.

FIG. 6 is a view illustrating an example of a microchannel 620 of a biological sample property measuring apparatus. The structure of the microchannel 620 of FIG. 6 may be applied to the example biosensors and the example biological sample property measuring apparatuses illustrated in FIGS. 1 through 5.

Referring to the example illustrated in FIG. 6, the microchannel 620 formed on a substrate 610 includes polydimethysiloxane (PDMS) layers 621 and 623 to prevent leakage of a biological sample 601. Referring to a cross-sectional view taken along the line A-A' of the example illustrated in FIG. 6, the PDMS layers 621 and 623 prevent a liquid type of the biological sample 601 from leaking. Although FIG. 6 illustrates the PDMS layers 621 and 623 in a continuous shape without interruption, in another example, the PDMS layers 621 and 623 are formed in an appropriate discontinuous shape in consideration of locations of the signal electrodes and the ground electrode.

Figure 7:
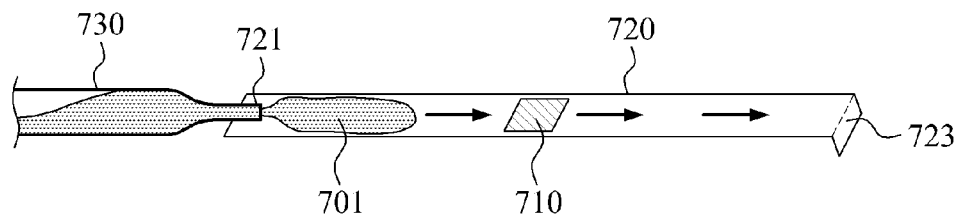
FIG. 7 is a view illustrating an example of injection of a biological sample and contact of the biological sample with a sensing unit of a biological sample property measuring apparatus.

FIG. 7 is a view illustrating an example of injection of a biological sample 701 and contact of the biological sample 701 with a sensing unit 710 of a biological sample property measuring apparatus. Referring to the example illustrated in FIG. 7, the biological sample 701 of a liquid type is provided to a channel 720 through an injection apparatus 730. The biological sample 701 of a liquid type flows from an input unit 721 of the channel 720 to an output unit 723 and, in an example, is in continuous contact with the sensing unit 710.

In a further example, obtaining an RF property indicator includes obtaining the RF property indicator iteratively from a time at which the biological sample 701 of a fluid type begins flowing on the sensing unit 710, and detecting a change in the iteratively obtained RF property indicator in real time. Since a function of the channel 720 is to provide a flow channel for the biological sample 701, the channel 720 is not limited to the shape of the example illustrated in FIG. 7. In other examples, the channel is provided in various shapes known to one of ordinary skill in the art, such as a curve or a serpentine shape.

Figure 8:
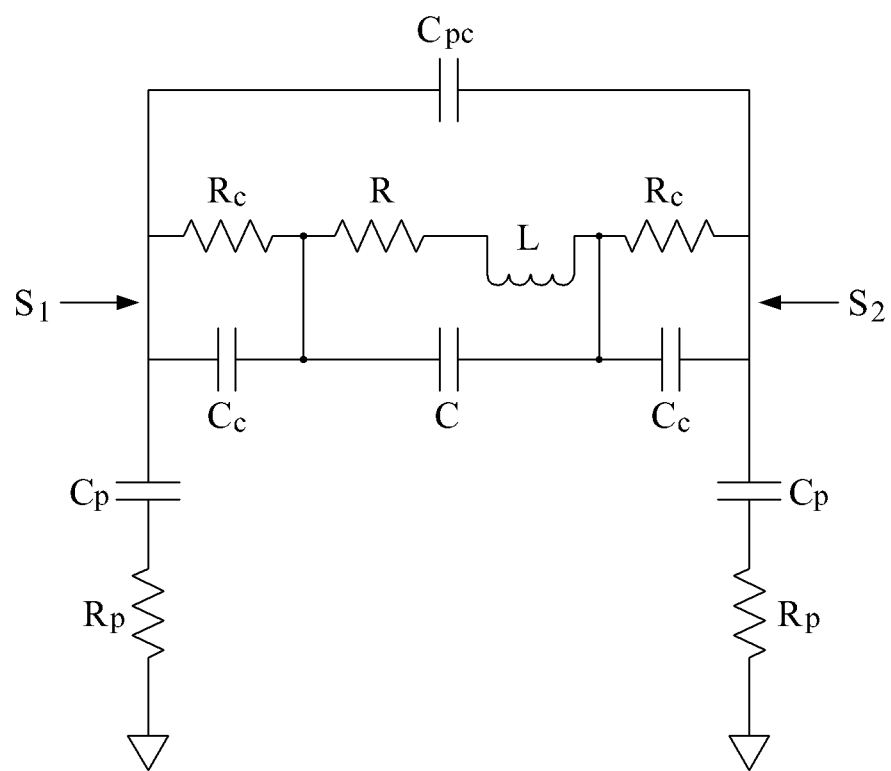
FIG. 8 is a diagram illustrating an example of an equivalent circuit model of a biosensor of a biological sample property measuring apparatus.

FIG. 8 is a diagram illustrating an example of an equivalent circuit model of a biosensor of a biological sample property measuring apparatus. The equivalent circuit model of FIG. 8 may correspond to, for example, an equivalent circuit model of the biosensor of the example biological sample property measuring apparatus 200 illustrated in FIG. 2.

Referring to the example illustrated in FIG. 8, in an aspect of RF analysis, the biosensor is modeled as an equivalent circuit including resistances $R_p$, R, and $R_c$, inductance L, and capacitors C, $C_c$, $C_p$, and $C_{pc}$. As shown in the equivalent circuit model, various property indicators may be obtained by measuring S-parameters between $S_1$ and $S_2$.

To improve sensitivity of the biosensor, noise needs to be removed through performing contact resistance analysis. That is, in an example, contact resistance analysis is performed by separating electrical properties unique to a material from contact characteristics between materials to enhance reactivity and sensitivity of the biosensor.

The units described herein may be implemented using hardware components or a combination of hardware and software components, such as, for example, processing devices. A processing device may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors. As used herein, a processing device configured to implement a function A includes a processor programmed to run specific software. In addition, a processing device configured to implement a function A, a function B, and a function C may include configurations, such as, for example, a processor configured to implement both functions A, B, and C, a first processor configured to implement function A, and a second processor configured to implement functions B and C, a first processor to implement function A, a second processor configured to implement function B, and a third processor configured to implement function C, a first processor configured to implement function A, and a second processor configured to implement functions B and C, a first processor configured to implement functions A, B, C, and a second processor configured to implement functions A, B, and C, and so on.

The software may include a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. In particular, the software and data may be stored by one or more computer readable recording mediums. The computer readable recording medium may include any data storage device that can store data which can be thereafter read by a computer system or processing device. Examples of the computer readable recording medium include read-only memory (ROM), random-access memory (RAM), CD-ROMs, magnetic tapes, floppy disks, optical data storage devices. In addition, functional programs, codes, and code segments for accomplishing the example embodiments disclosed herein can be easily construed by programmers skilled in the art to which the embodiments pertain based on and using the flow diagrams and block diagrams of the figures and their corresponding descriptions as provided herein.

A number of examples have been described above. Nevertheless, it should be understood that various modifications might be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A biological sample property measuring apparatus, comprising:
   a microchannel configured to provide a flow channel for a biological sample;
   a sensing unit on the flow channel, the sensing unit being configured to contact the biological sample;
   a first signal electrode configured to transmit a radio frequency (RF) signal to a first area of the sensing unit, the first signal electrode being in contact with the first area of the sensing unit;
   a second signal electrode configured to transmit the RF signal to a second area of the sensing unit, the second signal electrode being in contact with the second area of the sensing unit, and an RF property indicator between the first area of the sensing unit and the second area of the sensing unit being supplied to a probe unit; and
   a ground electrode configured to ground the RF signal.

2. The apparatus of claim 1, wherein the microchannel comprises a polydimethysiloxane (PDMS) layer configured to prevent leakage of the biological sample.

3. The apparatus of claim 1, further comprising:
   a substrate on which the microchannel, the sensing unit, the first signal electrode, the second signal electrode, and the ground electrode are formed.

4. The apparatus of claim 1, wherein the RF property indicator comprises one or more from the group consisting of an impedance, an inductance, a conductance, a capacitance, and a frequency.

5. The apparatus of claim 1, wherein the biomaterial comprises one or more from the group consisting of a cell, an organelle, a body fluid, deoxyribonucleic acid (DNA), ribonucleic acid (RNA), blood, plasma, glucose, glycated hemoglobin, cholesterol, a cancer cell, an antigen, an antibody, an influenza, protein, and a biological tissue.

6. The apparatus of claim 1, wherein the sensing unit comprises a mono-layered or multi-layered carbon-based material.

7. The apparatus of claim 1, wherein the probe unit comprises a first probe and a second probe, the first probe comprising a first tip and a second tip, the first tip of the first probe contacting the first signal electrode, the second tip of the first probe contacting the ground electrode, the second probe comprising a first tip and a second tip, the first tip of the second probe contacting the second signal electrode, the second tip of the second probe contacting the ground electrode.

8. The apparatus of claim 1, further comprising:
a measuring unit configured to supply the RF signal to the first signal electrode and the second signal electrode through the probe unit and receive the RF signal from the sensing unit through the probe unit.

9. A biological sample property measuring apparatus, comprising:
a microchannel configured to provide a flow channel for a biological sample;
a sensing unit on the flow channel, the sensing unit being configured to contact the biological sample;
a first signal electrode configured to transmit a radio frequency (RF) signal to a first area of the sensing unit;
a second signal electrode configured to transmit the RF signal to a second area of the sensing unit, an RF property indicator between the first area of the sensing unit and the second area of the sensing unit being supplied to a probe unit; and
a ground electrode configured to ground the RF signal,
wherein the probe unit comprises a first probe and a second probe, the first probe comprising a first tip and a second tip, the first tip of the first probe contacting the first signal electrode, the second tip of the first probe contacting the ground electrode, the second probe comprising a first tip and a second tip, the first tip of the second probe contacting the second signal electrode, the second tip of the second probe contacting the ground electrode.

10. A biological sample property measuring apparatus, comprising:
a microchannel configured to provide a flow channel for a biological sample;
a sensing unit on the flow channel, the sensing unit being configured to contact the biological sample;
a first signal electrode configured to transmit a radio frequency (RF) signal to a first area of the sensing unit;
a second signal electrode configured to transmit the RF signal to a second area of the sensing unit, an RF property indicator between the first area of the sensing unit and the second area of the sensing unit being supplied to a probe unit; and
a ground electrode configured to ground the RF signal,
wherein the probe unit includes a first probe and a second probe, the first probe including a first tip and a second tip, and the second probe including a first tip and a second tip, and
wherein the apparatus further comprises a measuring unit configured to supply the RF signal to the first signal electrode and the second signal electrode through the probe unit and receive the RF signal from the sensing unit through the probe unit.

* * * * *